(12) United States Patent
Bruno et al.

(10) Patent No.: US 6,324,900 B1
(45) Date of Patent: Dec. 4, 2001

(54) METHOD AND A DEVICE FOR OPTICALLY MEASURING THE TRANSPARENCY OF A LIQUID

(75) Inventors: Georges V. Bruno, Aix en Provence; Alain P. Minard, Le Clos, both of (FR)

(73) Assignee: Societe d'Etude et de Realisation d' Equipments Speciaux, Aix en Provence Cedex (FR)

(*) Notice: Subject to any disclaimer, the term of this patent is extended or adjusted under 35 U.S.C. 154(b) by 0 days.

(21) Appl. No.: 09/362,283

(22) Filed: Jul. 27, 1999

(30) Foreign Application Priority Data

Jul. 21, 1999 (EP) .................................. 994430014

(51) Int. Cl.$^7$ .................................................. G01N 21/00
(52) U.S. Cl. ............................................ 73/61.48; 356/928
(58) Field of Search ................................. 73/570, 53.01, 73/61.45, 61.49, 61.75, 64.53, 866.5, 431, 61.48, 64.43, 61.71; 356/237.1, 239.1, 446, 928

(56) References Cited

U.S. PATENT DOCUMENTS

| 5,377,005 | * 12/1994 | Meyer ................................. 73/61.71 |
| 6,134,952 | * 10/2000 | Garver et al. ...................... 73/61.71 |

FOREIGN PATENT DOCUMENTS

| 9015235 | 2/1991 | (DE) . |
| 0596231 | 5/1994 | (EP) . |
| 0634228 | 1/1995 | (EP) . |
| 1604691 | 12/1981 | (GB) . |
| 2052684 | 4/1977 | (JP) . |
| 1320449 | 12/1989 | (JP) . |
| 9800701 | 1/1998 | (WO) . |

OTHER PUBLICATIONS

Patent Abstracts of Japan vol. 14, No. 128 (P–1019), Mar. 9, 1990 & JP 01 320449 A (NEC CORP), Dec. 26, 1989.
Patent Abstracts of Japan vo. 001, No. 121 (E–053(, Oct. 13, 1977 & JP 52 052684 A (Chiyouonpa Kogyo KK), Apr. 27, 1977.

* cited by examiner

*Primary Examiner*—Richard A. Moller
(74) *Attorney, Agent, or Firm*—Ladas & Parry

(57) ABSTRACT

The technical field of the invention is that of searching for or analyzing materials, in particular liquids, by optical means. The method of optically measuring the transparency of a liquid uses a turbidity analyzer comprising at least one emitter of light passing through an optical interface piece providing an interface with the liquid illuminated in this way, and at least one measurement cell receiving a fraction of said light via a second optical interface piece, said fraction having traveled a given distance through said liquid. According to the method of the invention:

ultrasound waves are generated in the vicinity of the emitting and receiving optical/liquid interfaces of said optical pieces in contact with said liquid;

gaseous microcavities are thus created in the liquid and said interface surfaces are cleaned when said microcavities implode; and the emission of said ultrasound waves is stopped and the light received by the cell is measured.

20 Claims, 4 Drawing Sheets

METHOD AND A DEVICE FOR OPTICALLY MEASURING THE TRANSPARENCY OF A LIQUID

FIELD OF THE INVENTION

The present invention relates to a method and to a device for optically measuring the transparency of a liquid.

The technical field of the invention is the field of research or of analyzing materials, in particular liquids, by optical means.

The main application of the invention is to be able to determine the turbidity of water, essentially for monitoring its quality, and in particular by detecting matter in suspension or in an emulsion, such as hydrocarbons, which might be mixed therewith; the way in which this turbidity is determined is described in European and French standard NF, EN 2707 of 1994, which reproduces in full international standard ISO 7027 of 1990 and to which the person skilled in the art can refer for a better understanding of the present invention if that should be necessary.

BACKGROUND OF THE INVENTION

It is recalled in particular that in liquids, turbidity is the result of non-dissolved matter that is finely dispersed: it can be determined by measuring the decrease in the intensity of light flux as it passes through the liquid in which part of the light is absorbed, or by measuring the intensity of the light that is diffused, and in particular at 90°; light diffusion is a property of liquids which can be used for measuring such turbidity; the above-referenced European standard describes four optical methods for determining water turbidity to obtain information on site about surface water, potable water, and residual water. Since turbidity is an overall parameter for determining the level of pollution or the effectiveness of an industrial method, the present invention can have numerous applications, such as:

monitoring waste at the outlet from sewage stations, in terms of cloudy residual water;

monitoring sewage methods or industrial methods;

determining the quality of water in settling tanks, in river water, and in lake water;

detecting operating anomalies with filters, industrial separators;

monitoring industrial effluents, and in particular oil effluents;

monitoring deballasting by oil tankers; and monitoring discharges of bilge water into the sea by ships.

Numerous equipments have thus been developed to enable the turbidity in an aqueous medium to be measured, and more recently to comply with the above standard; some such apparatuses have constituted the subject matter of patent applications, such as application EP 596231 published on May 11, 1994 and international application WO 9800701 published on Jan. 8, 1998, which describe the combination of a nephelometer and a turbidimeter; it is recalled that nephelometry relates to measuring the concentration of an emulsion on the basis of its transparency.

Although those optical measurement apparatuses give full satisfaction concerning optically measuring the intensity of a given light after it has traveled a determined distance through the liquid under inspection, measurement proper is often spoilt by the fact that dirt such as oil can become deposited on the surfaces of the optical interfaces immersed in the liquid; the interfaces serve firstly to emit light into the liquid and secondly to receive light therefrom for measurement purposes: at present, methods and devices based on windshield-wiper principles are unsatisfactory and require assiduous maintenance.

OBJECTS AND SUMMARY OF THE INVENTION

The problem posed is thus to be able to guarantee that said optical interface surfaces are clean prior to taking each measurement so that the measurements are reliable, and to do so without using a mechanical device that requires intensive maintenance.

A solution to the problem posed is a method of optically measuring the transparency of a liquid by means of a turbidity analyzer comprising at least one emitter of light that passes through an optical interface piece such as a bar, an optical fiber, etc., providing an interface with the liquid that is illuminated in this way, and at least one measurement cell receiving a portion of said light via a second optical interface piece, which portion of light has traveled over a given distance through said liquid. According to the invention:

ultrasound waves are generated in all directions around the emitting and receiving optical/liquid interfaces of said optical pieces in contact with said liquid, thereby cleaning said interface surfaces or preventing them from becoming dirtied, in particular when gaseous microcavities created in this way in the liquid implode; and the emission of said ultrasound waves is stopped and a measurement is taken of the light received by the cell.

In a preferred embodiment, the device of the invention has a probe that can be immersed in the liquid, the probe having a liquid-proof housing that contains at least the light emitter, the measurement target, the associated optical interface pieces, and the ultrasound generator whose outlet has said two optical pieces integrated therein, thereby ensuring that they have an emission surface that is common therewith.

The result is novel methods and devices for measuring the transparency of a liquid and satisfying the problem posed, in particular by enabling the turbidity of said liquid to be measured with the desired degree of reliability. Unlike present turbidimeters, the device of the invention makes it possible in particular to perform high quality measurements on-site, regardless of the degree to which the liquid being analyzed is dirty: the emitted ultrasound prevents any development of microorganisms and also prevents any dirt being deposited on the optical interfaces.

In addition, the microcavitation caused by the ultrasound waves serves to homogenize the liquid medium by emulsifying it, in particular when it is confined in a measurement cell: this phenomenon makes it possible to make more reliable and to simplify detection of substances such as residual hydrocarbons in oil waste; otherwise these hydrocarbons tend to amalgamate in some portions of the liquid, thereby giving rise to false measurements since if such an amalgamation lies in the light beam, then the turbidity measurement taken will be much higher than the average turbidity of the medium, and conversely if an amalgamation is not in the beam, then the measurement will be much too small, and in both cases the measurement will not be representative of the mean turbidity of the liquid.

In addition, installation conditions are quite simple and adaptable to numerous sites, either merely by immersing a probe in the liquid, or by inserting optical and ultrasound interfaces in the wall of pipework or in a miniature emulsifying vessel, etc. . . . . .

Other advantages of the present invention could also be mentioned, but those mentioned above suffice to demonstrate the novelty and the advantage of the invention.

BRIEF DESCRIPTION OF THE DRAWINGS

The following description and figures relate to embodiments of the invention that are not limiting in any way. Other embodiments are possible within the ambit of the scope and the extent of the invention, and in particular.

- the disposition of the component elements of the immersible probe as shown can be changed;
- the elements required for the method of the invention need not be placed in a probe, but can be placed behind a wall of a receptacle, or of a hull, or of a length of pipework, etc. . . . ;
- the device or the method can be used for transparency measurements that are not solely turbidity measurements; or
- instead of measuring the light diffused by an incident beam, it is possible to measure directly the light of the emitted beam after it has traveled a given distance through the liquid, i.e. after some of it has been diffused and absorbed, in which case the receiver cell and its optical interface piece should be placed so as to face the emitted beam.

DETAILED DESCRIPTION

Figure 1:
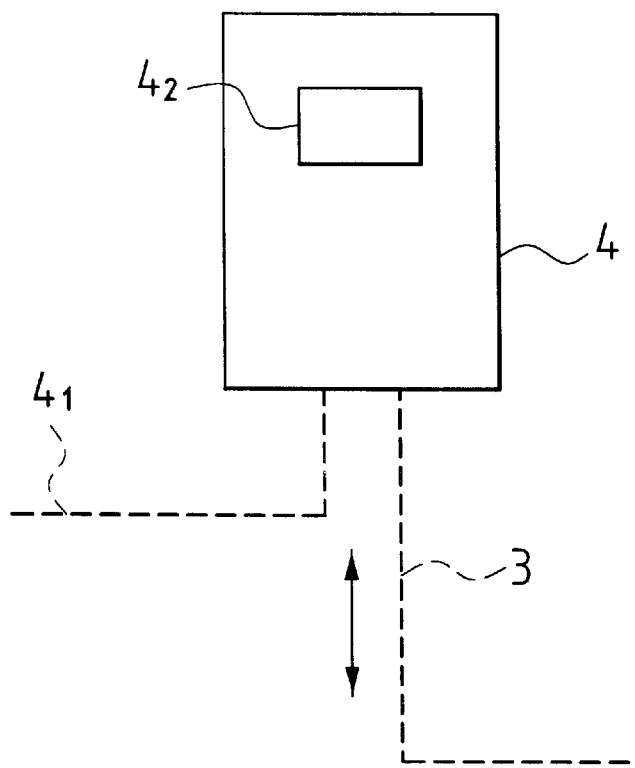
FIG. 1 is an overall view of a device of the invention, comprising an immersible probe in a vessel.
Figure 1:
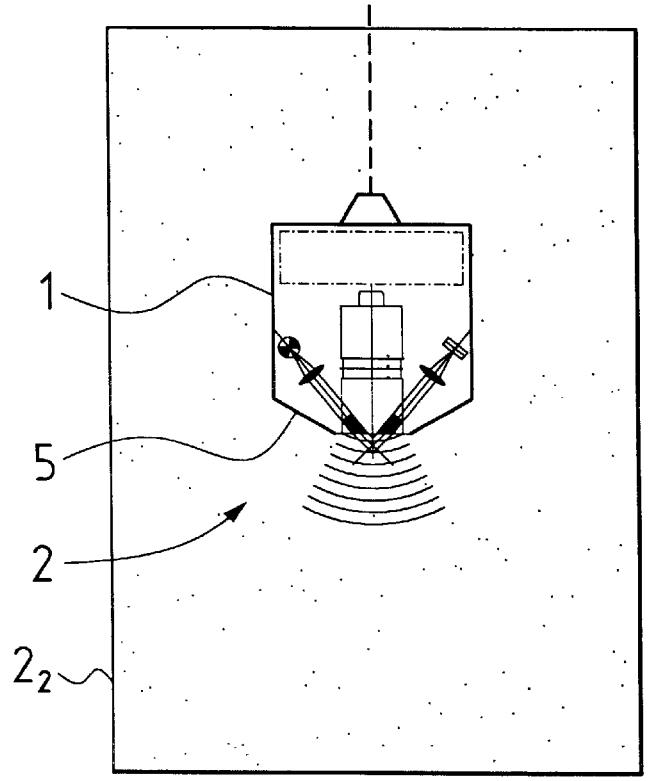

The device of the invention for optically measuring the transparency of a liquid 2 comprises a turbidity analyzer of conventional type comprising at least one emitter 7 of light $6_1$ passing through an optical interface piece $12_1$ providing an interface with the liquid 2 that is illuminated in this manner, and at least one measurement cell 9 receiving, via a second optical interface piece $12_2$ a portion of said light 10 that has traveled a given distance through said liquid 2.

In the invention, at least one ultrasound generator 15 whose outlet 13 is disposed in the vicinity of at least one of the above-defined optical interface pieces 12 emits ultrasound waves 21, that engage at least the interface surface 19, 20 of said piece where it is in contact with said liquid 2, the waves propagating through said liquid 2 in the vicinity of said surface 19, 20 and in all directions around it, covering at least said surfaces 19, 20.

The optical interface piece(s) $12_1$, $12_2$ is/are preferably secured to or even integrated in the outlet 13, and the emitting surface 19 and/or the receiving surface 20 is/are situated in the same plane 21 as said outlet 13.

In accordance with the invention, the optical interface pieces 12 are secured to the outlet 13 of the ultrasound generator so that the ultrasound is also generated from said surfaces 19 and 20.

Figure 3:
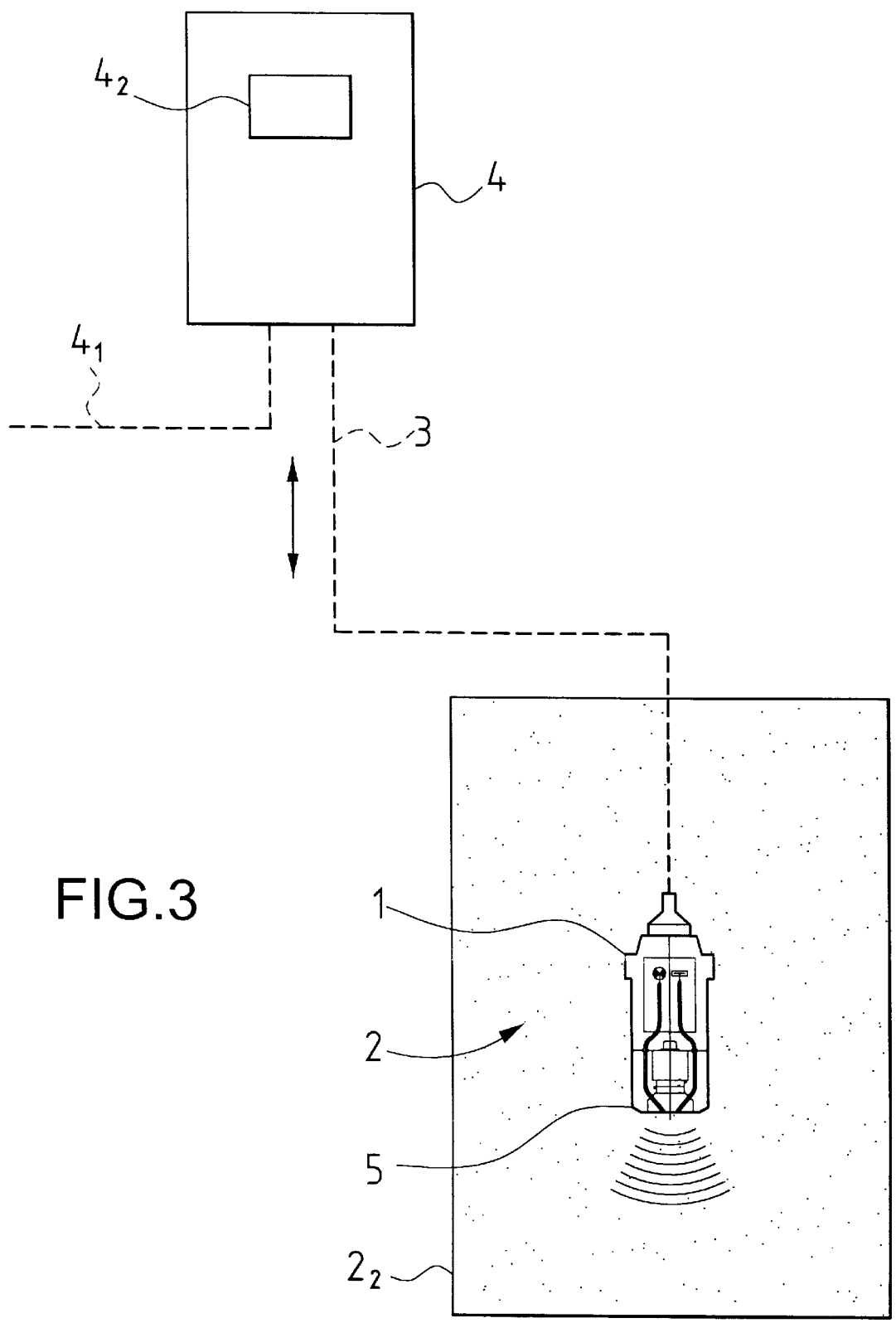
FIGS. 3 and 4 show a device of reduced size in which the optical pieces $12_1$ and $12_2$ are optical fibers.
Figure 4:
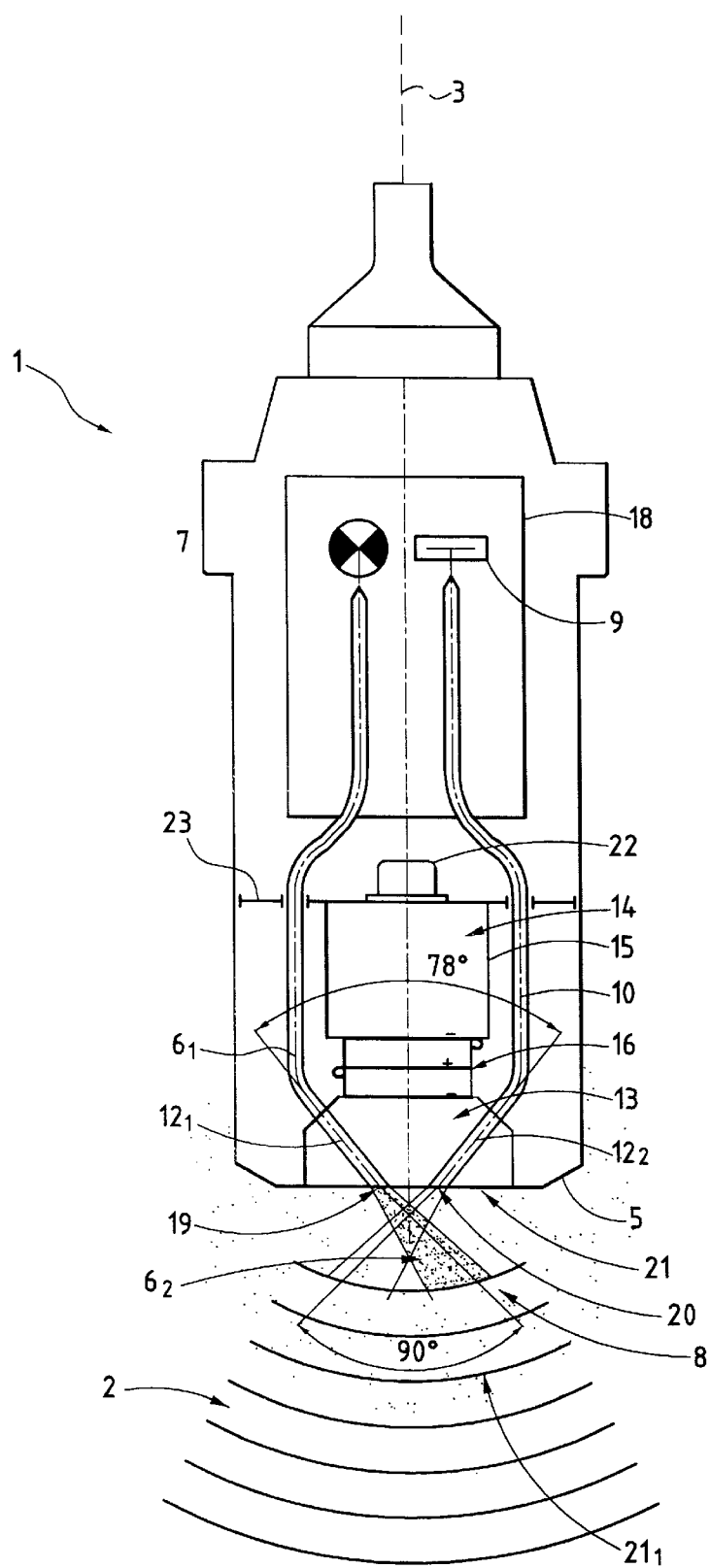

In an embodiment shown in FIGS. 3 and 4, the optical pieces are integrated in the outlet 13 by bores, in particular cylindrical bores, formed through said outlet.

When it is desired to measure the light 8 that is diffused laterally (and in particular at 90°) by the cone of light $6_2$ emitted by the emitter 7 into the liquid medium 2, said optical pieces $12_1$ and $12_2$ are spaced apart from each other and disposed at a common given angle relative to their respective optical interfaces 19 and 20 for emitting and receiving light in a common plane: the angle is determined so that the optical interface piece $12_2$ of the measurement cell 9 picks up the light 8 that is diffused at at least 90° relative to the light $6_2$ emitted into the liquid 2 through the optical interface piece $12_1$. Preferably, the optical pieces 12 are disposed at an angle α between their axes such that the light beams $6_1$ and 10 traveling along them are at an angle of at least 30°, and preferably 30°, 90°, or 180°, in the liquid 2, taking account of the refractive indices and coefficients between the material of said optical pieces and the liquid 2.

To take measurements in water using optical pieces $12_1$ and $12_2$ made of glass or glass fiber, the angle α is 78° for a 90° measurement, according to international standard ISO 2707.

Figure 2:
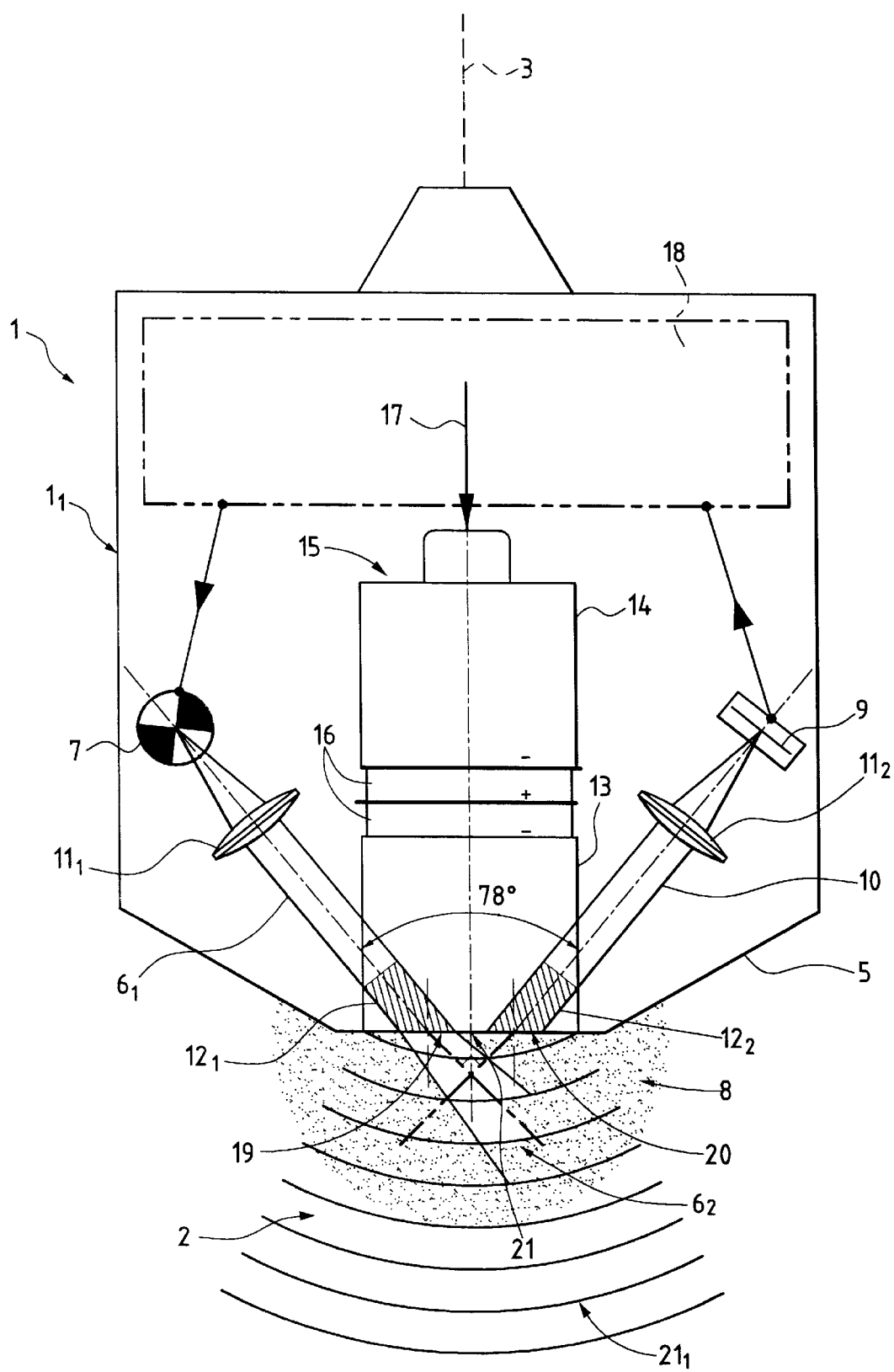
FIG. 2 is a simplified section view on a larger scale of the immersible probe shown in FIG. 1.

When the optical interface pieces are cylindrical bars of glass, as in FIG. 2, the light beam $6_1$ is concentrated on said optical piece $12_1$ by a lens $11_1$ which collimates the light emitted by the emitter 7. Similarly, the light beam 10 picked up through the optical interface piece $12_2$ passes through a converging lens $11_2$ to be concentrated on the measurement cell 9.

FIG. 3 shows an advantageous embodiment in which the optical interface pieces $12_1$ and $12_2$ providing the interfaces with the liquid 2 are themselves made of optical fibers. The use of optical fibers that are flexible makes it possible for them to pass in curved manner around the outlet 13 in which their ends are integrated so as to serve as light guides between the emitter 7 and the measurement cell 9 while occupying only a small amount of space. Because there is no need for the light to follow a rectilinear path, the emitter 7 and the measurement cell 9 can be close together. In addition, it is no longer necessary to use lenses $11_1$ and $11_2$.

The diameter of the optical fibers preferably lies in the range 1 mm to 4 mm. If the optical fibers are smaller in diameter, then measurement is unstable, while if the diameter is greater, then the fibers are no longer sufficiently flexible to accommodate such curving.

As an illustration, when using bars of glass that are 8 mm in diameter, the device shown in FIG. 1 has a diameter of 130 mm at the top end of the cone 5 surrounding the bottom surface 21 of the outlet 13, whereas by using optical fibers having a diameter of 2.5 mm, it is possible to reduce this diameter to 60 mm.

Because of its small size, the device shown in FIG. 4 makes it easier to perform measurements in a pipe of small diameter. In addition, because of the small diameter of the interface surfaces between the optical fibers and the liquid, the transcoder can operate at reduced energy, and in particular 30 W for fibers that are 3.5 mm in diameter instead of 60 W for the glass bars of FIG. 2, thereby ensuring that the probe vibrates less and withstands wear better.

The emitted light beam $6_1$ is preferably of infrared light having a wavelength lying in the range 700 nanometers (nm) to 1200 nm, for example about 850 nm, but it could also be ultraviolet light having a wavelength lying in the range 150 nm to 400 nm, or even visible light having a wavelength lying in the range 400 nm to 700 nm.

In conventional manner, and in addition to the outlet 13 for emitting ultrasound waves $21_1$, which outlet can be made of titanium so as to be as lightweight as possible, the ultrasound generator 15 also has a rear backing mass 14, preferably made of brass so as to be heavy, and piezoelectric ceramics 16 which are powered by contact with the electrodes and by using high voltage electricity 17 which generates vibrations at the desired frequency throughout the generator 15: the generator is secured firstly by a prestress screw 22 holding the generator assembly together, and secondly by any suspension device 23, for example resilient studs insulating it from the other elements constituting the device, and in particular from the leakproof housing $1_1$ of the probe 1 that is suitable for being immersed in the liquid 2 and that is shown in the accompanying figures by way of example.

Said housing $1_1$ houses at least one light emitter $6_1$, the measurement cell 9, the optical interface pieces 12, and the ultrasound generator 15: said probe 1 is connected to any appropriate link cable 3 leading to a measurement control unit 4 situated on the surface, e.g. above the vessel 22; said housing $1_1$ also houses at least one housing 18 providing an electrical interface between said link cable 3 and the three basic elements constituting said probe, namely the light emitter 7, the measurement cell 9, and the ultrasound generator 15 which includes the two optical interface pieces that are associated with the light emitter and with the measurement cell, respectively.

Since the ultrasound generator is suspended inside the housing $1_1$ of the probe 1, it is independent of the other electrical elements since only the light beams $6_1$ and 10 pass through its outlet 13, and the housing $1_1$ provides leakproofing around its ultrasound emitting surface 21. When the device of the invention is not installed in a probe comprising a closed housing, the above-described base elements and components thereof can be installed simply in a housing or behind a wall integrated in the wall containing the liquid that is to be monitored and isolating it from the remainder of an installation, e.g. the hull of a ship, the wall of a length of pipe, of a vessel, . . . .

In order to reduce the active area that might trap the air generated by the microcavitation that is created and that then implodes, thereby cleaning the surface 21 and thus the interface pieces, the housing $1_1$ of the probe preferably has a convex conical portion 5 surrounding the surface 21 of the ultrasound emitting outlet 13: said ultrasound waves are preferably at a frequency lying in the range 20 kHz to 50 kHz.

Said control unit 4 on the surface serves firstly to control and power the ultrasound generator 15 before performing any optical measurement, to power the light emitter 7, and to process the optical measurement taken by the receiver 9 after it has picked up the light diffused laterally and/or emitted directly into the axis of the emitter beam, after passing through the liquid 2, which signal from the sensor is preferably preamplified in the interface housing 18 situated within the probe 1; the control unit 4 can be powered by any available electricity source $4_1$ and the unit can have any appropriate device $4_2$ for displaying the result of the measurement; it is possible to process the measurements and the emission of ultrasound for two, four, or six probes by using multipath devices and multiplexing.

Advantageously, when the device of the invention is of small mass, as in FIG. 3, the suspension device 22 is constituted by a resilient membrane or "flector" made in particular out of PVDF in the form of a disk that is 1.5 mm thick. This resilient membrane serves better than resilient studs to reduce the transmission of vibration from the ultrasound generator 15 to the housing. Consequently, the vibration maximum occurs at the outlet 13.

The method and device of the invention for optically measuring the transparency of a liquid not only provides considerable savings, but is also technically advantageous in that it makes it possible, for example in a sewage works, both to take upstream measurements where the water is very cloudy, but also to take downstream measurements where the water is relatively clear.

The ranges over which the transparency and turbidity of the liquid 2 can be measured are a function of the medium, e.g. 0 to 100 NTU or 0 to 5000 NTU for very cloudy water (where NTU stands for "nephelometric turbidity unit" defined by standards in this field corresponding to measuring light diffused at 90° from the incident ray in the liquid), or 0 to 20 grams per liter (g/l) for sludge in which measurements are performed at 180° after absorption in the liquid.

What is claimed is:

1. A method of optically measuring the transparency of a liquid by a turbidity analyzer comprising an emitter of light passing through an optical interface piece providing an interface with the liquid being illuminated by said light, and a measurement cell receiving a portion of said light via a second interface of a second optical interface piece, said portion of said light having traveled a given distance through said liquid from the interface of the emitter to the interface of the measurement cell, wherein the method comprises:

generating ultrasound waves passing into the liquid and through said surfaces of said interfaces in contact with the liquid; thereby cleaning said interface surfaces and preventing said surfaces from becoming dirtied; said ultrasonic waves being generated by an ultrasonic wave generator and passing through an outlet of said generator to said liquid, supporting said optical interface pieces in said outlet of the ultrasonic generator so that the interface surfaces of said interface pieces are disposed in a common plane with an outer surface of said outlet of said ultrasonic wave generator and said ultrasonic waves traverse said interface surfaces of said interface pieces to directly clean said surfaces; and halting generation of said ultrasound waves and measuring the light received by the measured cell.

2. A method according to claim 1, wherein light picked up by the optical interface piece of the measurement cell is light that has diffused through at least 30° from the light emitted into the liquid through the optical interface piece of a said emitter.

3. A method according to claim 1, wherein light emitted from the light interface piece is diffused laterally at 90° into the liquid medium and the optical interface piece of the measurement cell receives the diffused light.

4. A method according to claim 1, wherein ultrasound waves are generated at frequencies of 20 kHz to 50 kHz.

5. A method according to claim 1, wherein the light emitted by the emitter is infrared light at a wavelength lying in the range 700 nm to 1200 nm.

6. A method according to claim 1, wherein said ultrasonic waves are generated along an axis of said outlet and said optical interface pieces converge towards said axis.

7. An optical device for measuring transparency of a liquid, the device comprising a turbidity analyzer comprising an emitter of light passing through an optical interface piece providing an interface with the liquid being illuminated by said light, and a measurement cell receiving a portion of said light through an interface surface of a second optical interface piece, said portion of light having traveled a given distance through said liquid, an ultrasonic generator for generating ultrasonic waves, said ultrasonic generator including an outlet through which said ultrasonic waves travel to said liquid, said optical interface pieces being supported by said outlet so that the interface surfaces of said interface pieces are disposed in a common plane with an outlet surface of said outlet and said ultrasonic waves traverse said interface surfaces of said interface pieces to directly clean said interface surfaces.

8. A device according to claim 7, including a probe immersible in the liquid, and having a housing that is leakproof and contains the light emitter, the measurement cell, said optical interface pieces, and the ultrasound generator.

9. A device according to claim 7, wherein the ultrasound generator is suspended inside a housing which provides leakproofing around the outlet surface of said outlet.

10. A device according to claim 8, wherein said housing includes a convex conical portion surrounding the outer surface of said outlet.

11. A device according to claim 7, wherein the optical interface pieces are disposed so that light beams which pass through them make an angle of at least 30° in the liquid.

12. A device according to claim 7, wherein said optical interface pieces are integrated in holes formed through said outlet.

13. A device according to claim 7, wherein said optical interface pieces are spaced apart from one another and are disposed in said outlet in a common plane, said optical interface pieces being at an angle so that light beams which pass through said optical interface pieces form an angle of at least 30°, in the liquid.

14. A device according to claim 7, wherein said optical interface pieces are optical fibers.

15. A device according to claim 14, wherein said optical fibers are flexible and extend in non-rectilinear manner outside the outlet so as to serve as light guides between the emitter and the measurement cell, in a compact configuration.

16. A device according to claim 14, wherein the diameter of the optical fibers lies in the range 1 mm to 4 mm.

17. A device according to claim 7, wherein the ultrasound generator includes a prestress screw holding a rear backing mass and the outlet together.

18. A device according to claim 14, wherein the ultrasound generator is fixed at a top end thereof in a housing by a suspension device constituted by a resilient membrane.

19. Apparatus according to claim 7, wherein said ultrasonic waves are generated along an axis of said outlet, said optical interface pieces converging towards said axis.

20. Apparatus according to claim 19, wherein said interface surfaces of the interface pieces of the emitter and the measurement cell are spaced from one another in the plane of the outlet surface.

* * * * *

UNITED STATES PATENT AND TRADEMARK OFFICE
CERTIFICATE OF CORRECTION

PATENT NO.     : 6,324,900 B1
DATED          : December 4, 2001
INVENTOR(S)    : Georges V. Bruno et al.

It is certified that error appears in the above-identified patent and that said Letters Patent is hereby corrected as shown below:

<u>Title page,</u>
Item [30], "994430014" should read -- 99430014.3 --.

Signed and Sealed this

Ninth Day of July, 2002

Attest:

Attesting Officer

JAMES E. ROGAN
Director of the United States Patent and Trademark Office